(12) United States Patent
Lamraoui et al.

(10) Patent No.: US 11,707,625 B2
(45) Date of Patent: Jul. 25, 2023

(54) TELEMETRY COMMUNICATION SYSTEM FOR AN IMPLANTABLE MEDICAL DEVICE

(71) Applicant: UROMEMS, Grenoble (FR)

(72) Inventors: Hamid Lamraoui, Grenoble (FR);
Marc Marien, La Tronche (FR);
Stephane Lavallee, St Martin D'Uriage (FR)

(73) Assignee: UROMEMS, Grenoble (FR)

( * ) Notice: Subject to any disclaimer, the term of this patent is extended or adjusted under 35 U.S.C. 154(b) by 350 days.

(21) Appl. No.: 16/649,094

(22) PCT Filed: Sep. 21, 2018

(86) PCT No.: PCT/FR2018/052304
§ 371 (c)(1),
(2) Date: Mar. 19, 2020

(87) PCT Pub. No.: WO2019/058064
PCT Pub. Date: Mar. 28, 2019

(65) Prior Publication Data
US 2020/0289824 A1  Sep. 17, 2020

(30) Foreign Application Priority Data
Sep. 22, 2017  (FR) ...................... 1758771

(51) Int. Cl.
*A61N 1/36* (2006.01)
*G16H 40/67* (2018.01)
(Continued)

(52) U.S. Cl.
CPC ..... *A61N 1/36128* (2013.01); *A61N 1/37217* (2013.01); *A61N 1/37282* (2013.01); *G16H 40/63* (2018.01); *G16H 40/67* (2018.01)

(58) Field of Classification Search
CPC ............ A61N 1/36128; A61N 1/37217; A61N 1/37282; G16H 40/63; G16H 40/67
See application file for complete search history.

(56) References Cited

U.S. PATENT DOCUMENTS 9,288,614 B1 * 3/2016 Young ................ A61N 1/37254
9,918,821 B2  3/2018 Lamraoui
(Continued)

FOREIGN PATENT DOCUMENTS

WO  2013/124362 A1  8/2013

OTHER PUBLICATIONS

International Preliminary Report on Patentability received for PCT Patent Application No. PCT/FR2018/052304, dated Apr. 2, 2020, 18 pages (8 pages of English Translation and 10 pages of Original Document).

(Continued)

*Primary Examiner* — Mallika D Fairchild
(74) *Attorney, Agent, or Firm* — Thomas | Horstemeyer, LLP

(57) ABSTRACT

The invention relates to a telemetry communication system for an implantable medical device (1) comprising a radiofrequency transceiver, comprising:
a remote controller (2) adapted to be used by a patient into whom said medical device (1) is implanted, said remote controller comprising a radiofrequency transceiver configured to communicate with said implantable medical device in a first frequency band (RF1), the transceiver of the remote controller (2) being paired with the transceiver of the implantable medical device (1),
a programming device (3) said implantable medical device adapted to be used by a practitioner, comprising a user interface (30), and configured to communicate
(Continued)

with the remote controller (2) through a wire connection or a wireless connection in a second frequency band (RF2) different from the first frequency band, the programming device (3) being configured to, when said connection is established between the remote controller (2) and the programming device (3), establish a communication between the implantable medical device and the programming device through the remote controller.

17 Claims, 7 Drawing Sheets

(51) Int. Cl.
  *G16H 40/63* (2018.01)
  *A61N 1/372* (2006.01)

(56) References Cited

U.S. PATENT DOCUMENTS

| | | | |
|---|---|---|---|
| 2002/0082665 A1* | 6/2002 | Haller | A61N 1/37264 607/60 |
| 2002/0123673 A1 | 9/2002 | Webb et al. | |
| 2010/0137962 A1* | 6/2010 | Moffitt | A61N 1/372 607/116 |
| 2011/0057037 A1* | 3/2011 | Frysz | G16H 10/60 235/375 |
| 2012/0035686 A1 | 2/2012 | Petersen et al. | |
| 2013/0147622 A1* | 6/2013 | LaLonde | G16H 10/60 340/539.12 |
| 2014/0228912 A1* | 8/2014 | Seim | A61N 1/37247 607/59 |
| 2014/0273824 A1* | 9/2014 | Fenner | A61B 5/0031 455/41.1 |
| 2016/0303313 A1* | 10/2016 | Burke | A61M 5/14276 |

OTHER PUBLICATIONS

International Search Report and Written Opinion received for PCT Patent Application No. PCT/FR2018/052304, dated Dec. 19, 2018, 20 pages (8 pages of English Translation and 12 pages of Original Document).

Preliminary Research Report received for French Application No. 1758771, dated Jun. 11, 2018, 3 pages (1 page of French Translation Cover Sheet and 2 pages of original document).

* cited by examiner

TELEMETRY COMMUNICATION SYSTEM FOR AN IMPLANTABLE MEDICAL DEVICE

FIELD OF THE INVENTION

The present invention relates to a telemetry communication system for an implantable medical device.

BACKGROUND OF THE INVENTION

There are numerous medical devices implantable into a patient to fulfil a function in the patient's body, for example to overcome a dysfunction of a natural organ.

Within this scope, it is usually necessary to be able to communicate with the implanted device (also called an implant in the following text). One purpose of this communication can be to drive the operation of the implanted device (for example to activate or deactivate it, or to implement a particular operating mode), to configure its internal parameters or to obtain information from the device (for example to know the state of the device or to obtain the patient's parameters measured by sensors implanted with the device).

To that end, it is known to equip the patient with a remote controller.

For example, in the case of neurostimulation, the implant consists of a stimulator and an electrode which are implanted under the patient's skin, so as to enable electrical pulses to be applied to determined areas of the spinal cord. Generating pulses is controlled by a remote controller held by the patient, which has to place the remote controller on his/her skin in the vicinity of the stimulator in order to actuate the stimulator by induction.

For ease of use, new generation implants are equipped with radiofrequency (RF) chips.

To allow bidirectional communication between said remote controller and the implanted device, each of them comprises a radiofrequency (RF) chip comprising both an RF wave transmitter and receiver.

Such a remote controller thus enables the patient to control some functions of the implanted device in everyday life, for example to activate or deactivate it if necessary. The remote controller also enables the patient to obtain information on the state of the device, for example the state of charge of an energy source implanted with the device.

However, this remote controller has limited functionalities and does not enable, for example, the operation of the implanted device to be programmed.

Such an intervention on the operation of the implant device is reserved for the practitioner.

This intervention can occur for example in the operating suite, when the device is implanted into the patient, to program the device as a function of the patient's characteristics.

This intervention can occur later during the patient's visits at the practitioner's, during which the practitioner recovers data from the implant to analyse them and possibly reprograms the implant.

To that end, the practitioner has a programming device (also called a programmer in the following text) which has more functionalities than the patient's remote controller. This programmer thus usually comprises an interface enabling a user to input new operating parameters of the patient and to view the implant data.

It is therefore necessary to establish a communication between the programmer and the implant, which implies the following considerations.

First, it should be ensured that no non-authorized third party can communicate with the implant, for reasons of patient's safety (take over of the implant by the third party) or respect of his/her medical data (recovered from the implant).

Besides, it should be ensured that the practitioner communicates with the proper implant. Given the range distance of the RF transceivers which is typically a few metres, if several implants are in the proximity of the programmer, there is a confusion risk resulting in the communication with a different implant from that with which it is desired to communicate.

There are also requirements in terms of use of the programmer. Indeed, the practitioner should be able to use the programmer in a simple way and with a minimum of actions.

Moreover, the programmer must be able to be used in the operating suite, to program the implant before or during the implantation. As it is necessary to keep the programmer at a distance from the sterile field, an RF communication can be degraded given the wave reflection in the operating suite. Moving the programmer closer to the implant would require to place the programmer into a sterile cover, which raises practical problems.

BRIEF DESCRIPTION OF THE INVENTION

One purpose of the invention is to overcome the above-mentioned problems and to design a bidirectional communication system for an implant with the patient's remote controller and the practitioner's programmer which is secure and of a good quality.

In accordance with the invention, it is provided a telemetry communication system for an implantable medical device comprising a radiofrequency transceiver, comprising:
- a remote controller adapted to be used by a patient into whom said medical device is implanted, said remote controller comprising a radiofrequency transceiver configured to communicate with said implantable medical device in a first frequency band, the transceiver of the remote controller being paired with the transceiver of the implantable medical device,
- a programming device for programming said implantable medical device adapted to be used by a practitioner, comprising a user interface, and configured to communicate with the remote controller through a wire connection or a wireless connection in a second frequency band different from the first frequency band,
- the programming device being configured to, when said connection is established between the remote controller and the programming device, establish a communication between the implantable medical device and the programming device through the remote controller.

The first frequency band is a frequency band dedicated to medical devices, distinct from the frequency band intended for the consumer applications, which enables communications safety between the implantable medical device and the remote controller to be ensured.

In contrast, the second frequency band is a frequency band dedicated to consumer applications, which provides a large flexibility in establishing a communication between the programming device and the remote controller. Alternatively, such a flexibility can be provided by implementing a wire connection between the programming device and the remote controller. In any case, the communications safety between the programming device and the implantable medical device is provided by the remote controller which is essential to establish these communications.

By "practitioner", it is meant any person of the medical profession entitled to program the implant and/or query data recorded in the implant, such as for example a surgeon, a doctor, or a nurse.

According to one embodiment, the programming device comprises a housing for plugging in the remote controller.

Advantageously, the programming device comprises a reader adapted to read a pairing code associated with the implantable device and/or a pairing code associated with the remote controller.

According to one embodiment, the pairing code comprises a bar code.

The reader can be of the optical type and/or near field communication type, for example of the RFID or NFC type.

According to one embodiment, the connection between the remote controller and the programming device is a wireless connection, for example of the Bluetooth, Wi-Fi or infrared type.

Alternatively, the connection between the programming device and the remote controller is a wire connection, the programming device and the remote controller comprising respective connectors adapted to cooperate with each other.

According to one embodiment, each of the remote controller and of the programming device comprises a microcontroller and the connection between the remote controller and the programming device comprises a data transmission between said microcontrollers.

According to one embodiment, the programming device comprises a microcontroller and the connection between the remote controller and the programming device comprises a data transmission between said microcontroller and the transceiver of the remote controller.

According to one embodiment, the remote controller comprises a microcontroller and the connection between the remote controller and the programming device comprises a data transmission between said microcontroller and the user interface of the programming device.

The programming device is advantageously configured to display information relating to the state of the remote controller on the user interface when the remote controller is connected with said programming device.

According to one embodiment, the connection between the remote controller and the programming device comprises supplying energy to the remote controller through the programming device.

Another object of the invention relates to a method for communicating between an implantable medical device comprising a radiofrequency transceiver and a programming device of a system such as previously described, characterised in that it comprises establishing a connection between the remote controller of said system and the programming device and establishing a communication between the programming device and the implantable medical device through the remote controller.

According to one embodiment, said method comprises, prior to establishing the communication between the programming device and the implantable medical device, a step of pairing the remote controller with the implantable medical device comprising:
reading a pairing code of the remote controller by the programming device, or inputting said code on the programming device,
establishing a connection between the remote controller and the programming device,
reading a pairing code of the implantable medical device by the programming device, or inputting said code on the programming device, and sending said code to the remote controller,
validating the pairing with said codes.

According to one embodiment, in the absence of the remote controller paired with the implantable medical device, another remote controller unpaired with said implantable medical device is used and the following steps are implemented:
reading a pairing code of said other remote controller by the programming device, or inputting said code on the programming device,
establishing a connection between said other remote controller and the programming device,
reading the pairing code of the implantable medical device, or inputting said code on the programming device, and sending said code to said other remote controller,
confirming, by a user, a pairing control order.

According to one embodiment, in the absence of the remote controller paired with the implantable medical device, another remote controller unpaired with said implantable medical device is used and the following steps are implemented:
reading a pairing code of said other remote controller by the programming device, or inputting said code on the programming device,
establishing a connection between said other remote controller and the programming device,
detecting at least one medical device within reach of said other remote controller,
selecting, by a user, the implantable medical device with which said other remote controller has to be paired,
confirming, by the user, a pairing control order.

According to one particular embodiment, confirming the pairing control with the selected implantable medical device comprises performing a series of taps according to a predetermined code on the patient's skin facing the implantable medical device, said code being detected by a sensor of said device.

According to one embodiment, in the absence of the remote controller paired with the implantable medical device, a so-called general purpose remote controller is used, configured to communicate with any implantable medical device of the same type and the following steps are implemented:
reading a pairing code of said general purpose remote controller by the programming device,
establishing a connection between said general purpose remote controller and the programming device,
detecting at least one medical device within reach of said general purpose remote controller,
selecting, by a user, the implantable medical device with which the connection has to be made,
confirming, by a user, the connection between said implantable medical device and the programming device.

According to one particular embodiment, confirming the connection between the selected implantable medical device and the programming device comprises performing a series of taps according to a predetermined code on the patient's skin facing the implantable medical device, said code being detected by a sensor of said device.

BRIEF DESCRIPTION OF THE DRAWINGS

Further characteristics and advantages of the invention will appear upon reading the following detailed description, with reference to the appended drawings in which.

Identical reference marks from one figure to the other refer to identical components or fulfilling the same function.

DETAILED DESCRIPTION OF EMBODIMENTS OF THE INVENTION

Figure 1A:
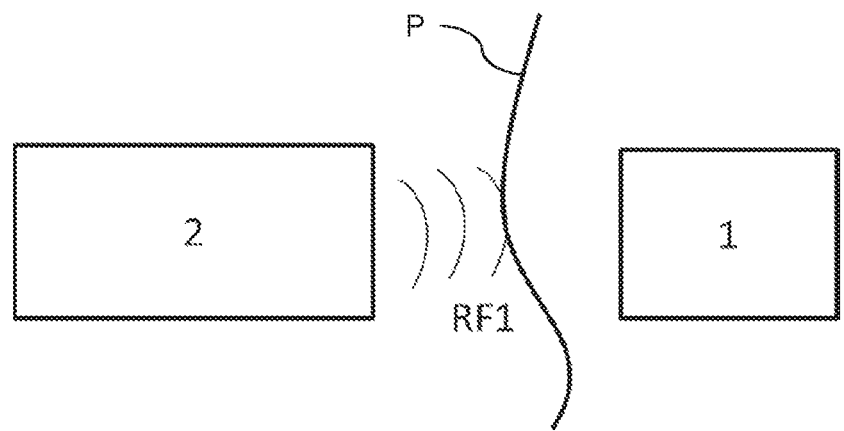
FIGS. 1A to 1C are schematic diagrams of the communication of the implant with the programming device and the remote controller, according to different embodiments of the invention.
Figure 1B:
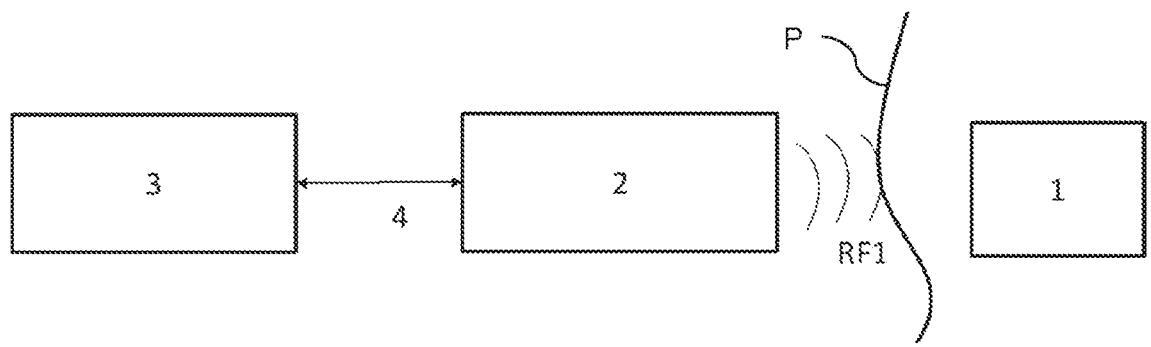
Figure 1C:
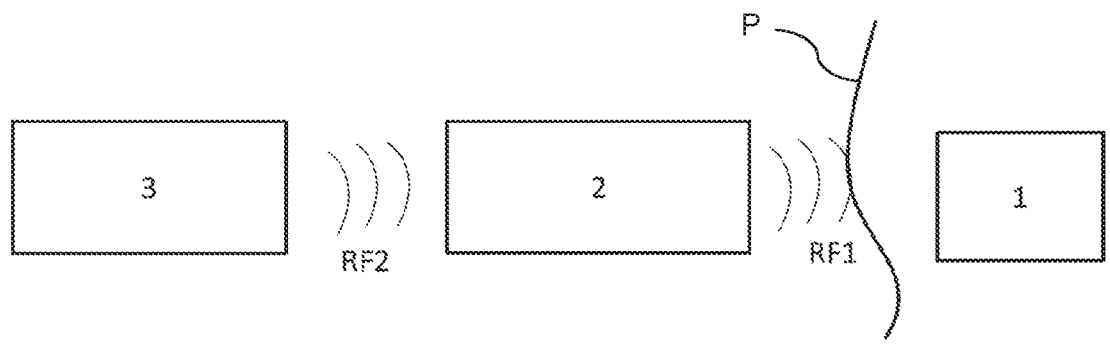

FIGS. 1A to 1C are schematic diagrams of the communication system allowing communication of the implant with the programming device and remote controller. In these figures, the patient (only a part of whose skin is represented) is referred to by the mark P.

By "communication", it is meant the data transmission between two devices.

Said communication is bidirectional, that is it comprises the transmission of signals to and from the implant, for example to program the implant or recover data therefrom.

As explained in further detail below, in this system, only the remote controller is able to communicate with the implant by telemetry. To that end, the remote controller is paired with the implant with a specific code, and the communication is performed in a determined frequency band, denoted as RF1 in the following of the description. Said frequency band is advantageously specific to implantable medical devices, and enables interference with other types of radiofrequency devices (other than implants) to be limited during data exchange between the implant and the remote controller. Thus, the frequency band is advantageously MICS (for Medical Device Radiocommunications Service) band.

Regarding the programming device, it cannot directly communicate with the implant but can do so with the remote controller, which relays communication.

The communication between the programming device and the remote controller can be established either in a wire way, or by wireless connection. In the case of a wireless connection, the communication between the programming device and the remote controller is made in a frequency band denoted as RF2 in the following text of the description, different from the frequency band RF1. Advantageously, the frequency band RF2 is a standard frequency band (that is intended for the consumer market), not specific to the implant.

In the case where the remote controller is not available during the patient's visit at the practitioner's, the communication between the programming device and the implant can be established as follows.

The practitioner can have a so-called "general purpose" remote controller, that is similar to the patient's remote controller but not paired with the latter, and able to communicate with the programming device and with any implant of the same type as that implanted into the patient.

In order to establish a communication with the implant and be sure that the practitioner communicates with the proper implant, a checking procedure must be implemented. For example, before a communication session, the practitioner has to check the serial number of the implant and/or enter a password. Possibly, if the implant can be controlled by a tap (as described in document WO 2013/124362 for example), the practitioner can perform a series of taps according to a predetermined code on the patient's skin facing the implant, which is detected by a sensor of the implant and recognised as a validation control.

FIG. 1A illustrates a situation in which the patient uses the remote controller 2 to communicate with the implant 1.

FIG. 1B illustrates a situation in which the programming device 3 communicates with the implant 1 through the remote controller 2. In this embodiment, the connection between the remote controller 2 and the programming device 3 is wire (depicted by the wire 4).

FIG. 1C also illustrates a situation in which the programming device 3 communicates with the implant 1 through the remote controller 2. In this embodiment, the connection between the remote controller 2 and the programming device 3 is wireless (schematised by the waves RF2).

Figure 2:
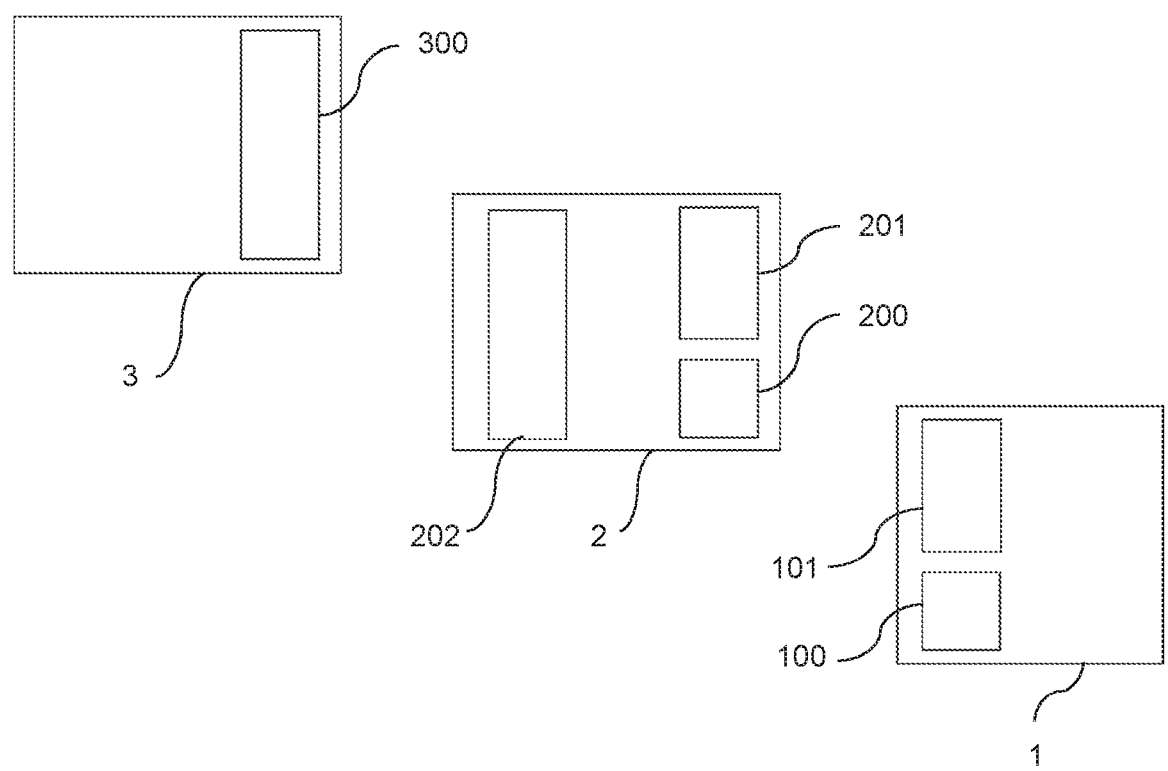
FIG. 2 is a schematic diagram of the architecture of the communication system according to the invention.

FIG. 2 schematically illustrates the general architecture of the system.

Implant

The implant can be any medical device implantable into the patient's body, and intended to communicate with means external to the patient. For example, the implant can be an artificial sphincter, a neurostimulator, etc.

The implant is provided with a single pairing code (or secrete key), different from the pairing codes of other implants. Said pairing code (referred to by mark 100 in FIG. 2) can be for example but in a non-limiting way a serial number, a bar code (for example a QR code), an NFC (for Near Field Communication) code, etc. This code can be placed on the implant itself or on the package in which it is delivered before implantation, this package being specific to the implant.

This pairing code is adapted to be read by the programming device if the latter comprises a reading system adapted to read the pairing code. Alternatively, in particular in the case where the pairing code consists of digits, letters and/or other typographic marks, it can be manually input by the practitioner by means of the user interface of the programming device.

The implant further comprises a radiofrequency transceiver (referred to by mark 101 in FIG. 2) allowing communication with the remote controller in the frequency band RF1. Such a transceiver is known per se and will therefore not be described in detail here, those skilled in the art being able to select it from transceivers available on the market.

The implant further comprises a memory into which the pairing code of the remote controller, as well as data relating to the patient can be recorded.

Remote Controller

The remote controller is a device for use by the patient, generally comprising one or several buttons associated with particular functionalities.

Figure 3A:
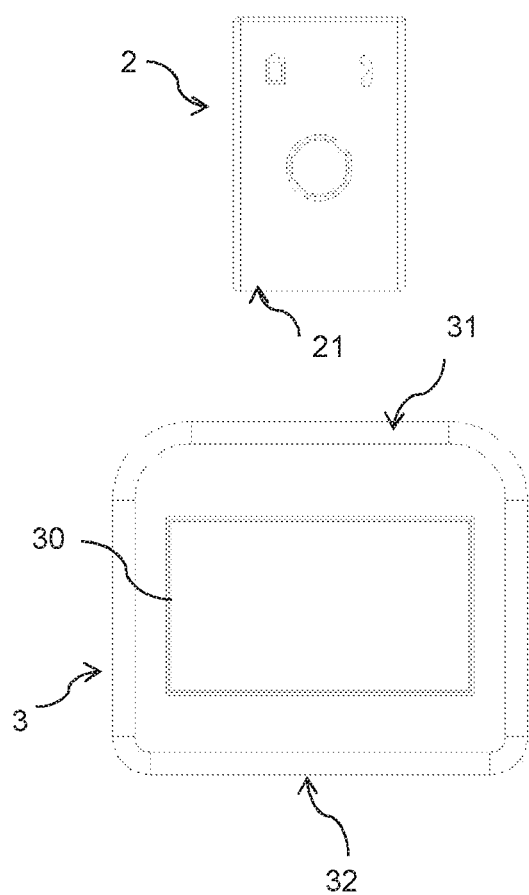
FIGS. 3A-3B, 4A-4B and 5A-5B illustrate three embodiments of a wire connection between the remote controller and the programming device, FIG. 6 schematically illustrates a wireless connection between the remote controller and the programming device.
Figure 3B:
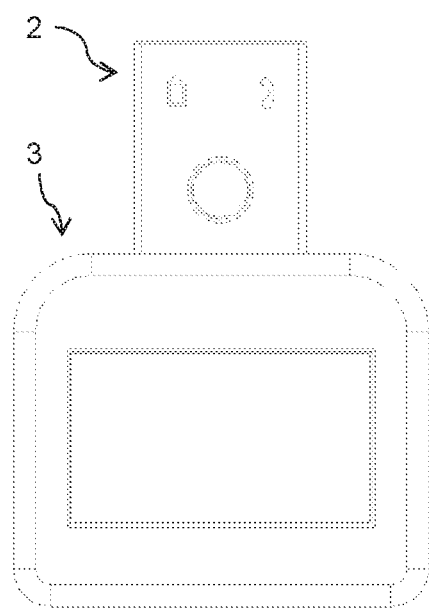
Figure 4A:
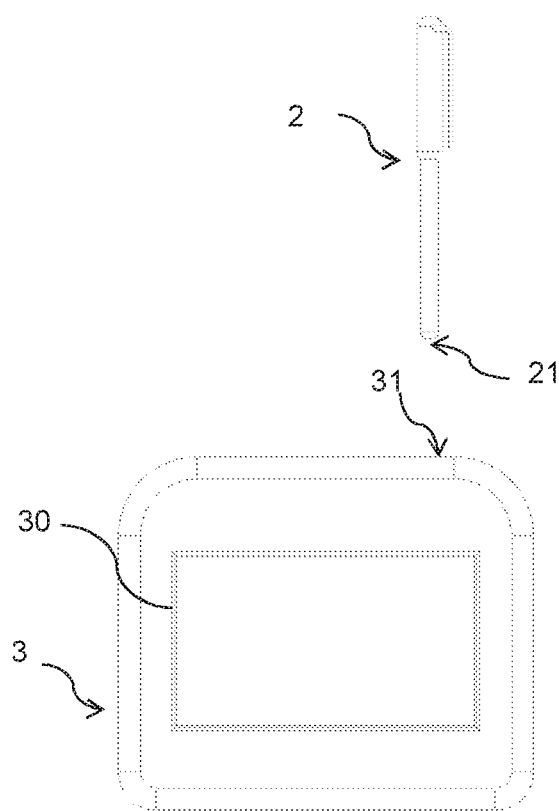
Figure 4B:
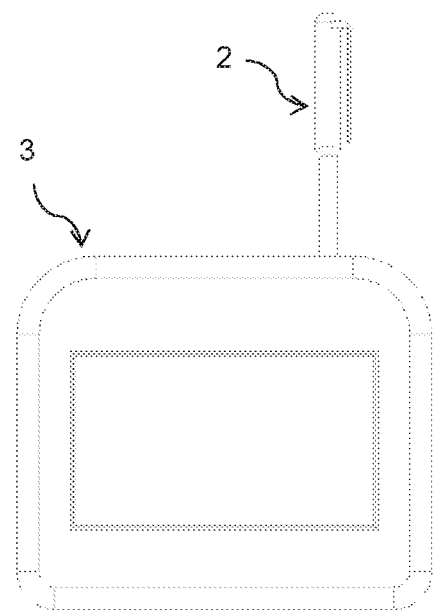

The remote controller can take any adapted shape especially from the ergonomic point of view (ease of use, compactness, etc.). For example, in order to be easily carried, the remote controller can be substantially of the format of a credit card (ref. FIGS. 3A-3B), or of a shape similar to that of a pen (ref. FIGS. 4A-4B). Thus, it can be easily slipped into a pocket of a cloth or into luggage. Of course, the invention is not limited to the shapes illustrated in the appended drawings.

The remote controller is provided with a pairing code (referred to by mark 200 in FIG. 2). Said pairing code can be for example but not limited thereto, a serial number, a bar code (for example a QR code), an NFC code, etc. This code can be placed on the remote controller itself or on the package in which it is delivered before implantation, this package being specific to the remote controller.

This pairing code is adapted to be read by the programming device if the latter comprises a reading system corresponding to the pairing code, or, especially in the case where the pairing code consists of digits, letters and/or other typographic marks, it can be input manually by the practitioner by means of the user interface of the programming device.

The remote controller further comprises a radiofrequency transceiver (referred to by mark 201 in FIG. 2) enabling a communication with the implant in the frequency band RF1. Such a transceiver is known per se and will therefore not be described in further detail here, those skilled in the art being able to select it from the transceivers available on the market.

The remote controller also comprises a microcontroller, as well as a connection means (referred to by mark 202 in FIG. 2) with the programming device, different wire or wireless embodiments of which are described below.

The remote controller advantageously comprises a memory into which the pairing code of the implant, as well as data recovered from the implant can be recorded.

Programming Device

The programming device comprises a user interface, through which the practitioner can connect to the remote controller (which in some cases can require to input of a password) and carry out various operations (programming or data recovery) on the implant.

The programming device can comprise a reader based on a technology adapted to the pairing code of the implant and/or, optionally, the remote controller. For example, if the pairing code of the implant is a QR code, the programming device comprises an optical reader adapted to read such a QR code. The reader can also be of the RFID or NFC type.

The programming device comprises a microcontroller, as well as a connection means (referred to by mark 300 in FIG. 2) with the programming device, different wire or wireless embodiments of which are described below.

Advantageously, the programming device is in the form of a touchscreen tablet.

The programming device can possibly comprise Wi-Fi or GSM type communication means in order to be able to transfer recovered data onto a server.

Connection with the Programming Device and the Remote Controller

Wire Connection

According to one embodiment, the connection between the programming device and the remote controller can be carried out by a direct engagement of two complementary connectors, one belonging to the programming device, the other to the remote controller. Any connector type can be used, in particular USB (for Universal Serial Bus) connectors.

The connector of the programming device is advantageously disposed in a housing adapted to accommodate the remote controller.

FIGS. 3A-3B thus illustrate an embodiment in which the programming device 3 comes as a tablet comprising a touch screen 30 and the remote controller 2 has a flat rectangular shape of the "credit card" type, comprising a connector 21 on its width. A face of the programming device comprises a housing 31 as a slot with a dimension adapted to the width and thickness of the remote controller, a complementary connector (not illustrated) to that of the remote controller being arranged at the bottom of said housing 31. Possibly, the programming device can have, on another face, a housing 32 for the "general purpose" remote controller. FIGS. 3A and 3B show the programming device 3 and the remote controller 2 disconnected and connected respectively.

FIGS. 4A-4B illustrate an embodiment in which the programming device 3 is in the form of tablet comprising a touch screen 30 and the remote controller 2 has a cylindrical shape of the "pen" type, comprising a connector 21 at one end. A face of the programming device comprises a housing 31 as a circular hole adapted to the diameter of the remote controller 2, a complementary connector to that of the remote controller (not illustrated) being arranged at the bottom of said housing 31. FIGS. 4A and 4B present the programming device 3 and the remote controller 2 disconnected and connected respectively.

Figure 5A:
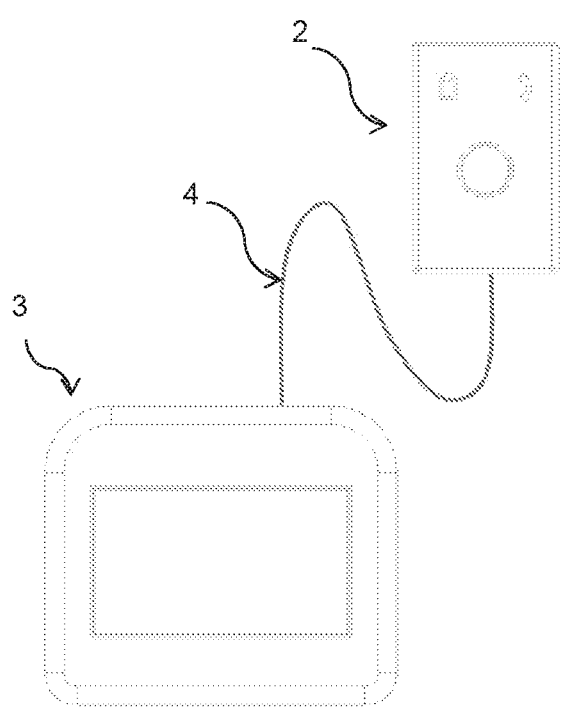
Figure 5B:
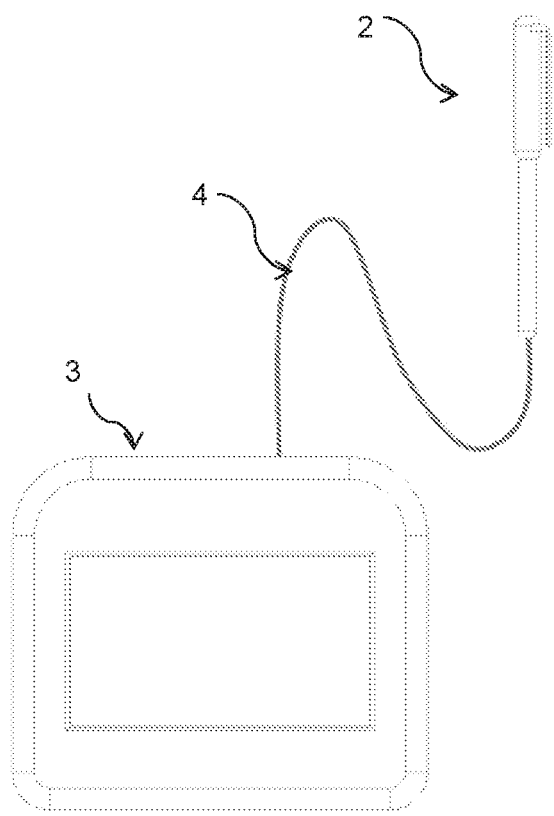

Alternatively, being illustrated in FIGS. 5A-5B, the connection between the programming device and the remote controller can be made by means of an electric cable 4 plugged between connectors respectively located on the programming device 3 and the remote controller 2.

The communication between the remote controller and the programming device can be carried out in different ways, for example:
- between the microcontroller of the programming device and that of the remote controller;
- between the microcontroller of the programming device and the transceiver of the remote controller;
- between the user interface of the programming device and the microcontroller of the remote controller; for example, if the programming device comprises a touch interface which is only functional when the remote controller is connected to the programming device.

Those skilled in the art will be able to use any adapted communication protocol, such as for example, but not limited thereto: SPI, I2C, RS232, CAB, analogue, etc.

Wireless Connection

Figure 6:
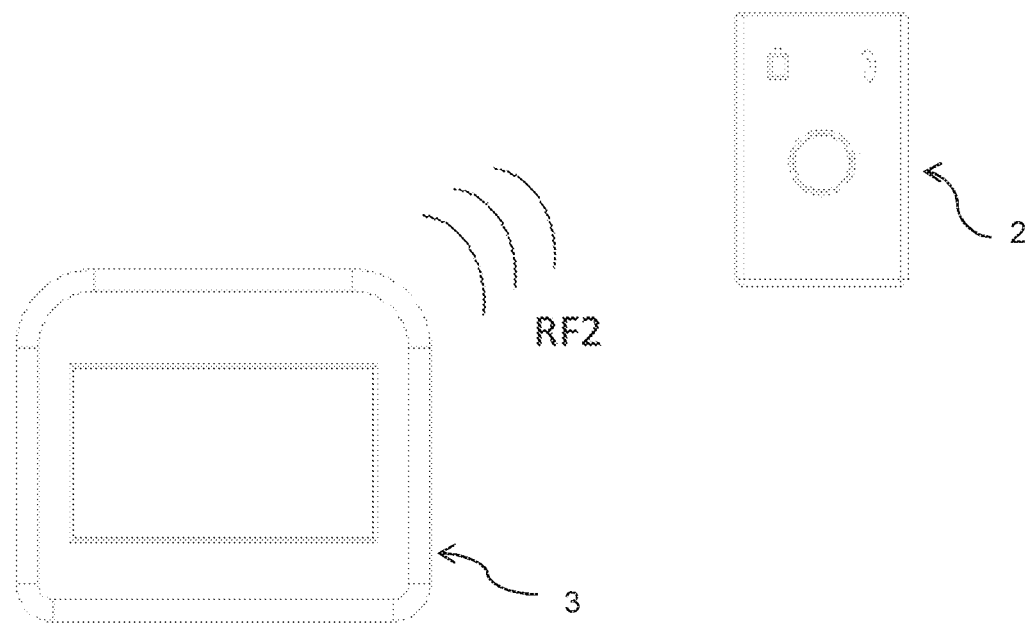

According to one embodiment illustrated in FIG. 6, the remote controller 2 and the programming device 3 can comprise wireless connection means, in the frequency band RF2.

Those skilled in the art will be able to use any communication protocol of their choice, such as for example but in a non-limiting way: Bluetooth (4.0, BLE, 5, . . . ), Wi-Fi, Wi-Fi LowEnergy, Infrared, Zigbee, RF4CE, etc.

In the case of a wireless connection, a pairing between the programming device and the remote controller is necessary. Those skilled in the art will choose any suitable pairing technology, such as: QR code, Datamatrix, RFID, NFC, iBeacon, Bokode (non-exhaustive list).

Like in the embodiment of FIGS. 3A and 4A, the programming device can comprise a housing for plugging in the remote controller, even if in this case the housing does not contain any connector for the communication between the remote controller and the programming device, but is used as a support for the remote controller.

In any case (wire or wireless connection), the connection between the remote controller and the programming device advantageously allows diagnostic of the state of the remote controller (charge level of the remote controller battery, alarm generation in case of system failure, evaluation of the communication quality, recovery of data contained in the memory of the remote controller, etc.) to be carried out.

Furthermore, the connection of the remote controller to the programming device may enable the remote controller to be electrically supplied during the visit phase.

Communication Procedure

Before and/or During the Implantation

Before and/or during the implantation, a remote controller intended for the patient is supplied to the practitioner or any other member of the medical staff. As above indicated, the remote controller and the implant are each provided with a pairing code.

Figure 7:
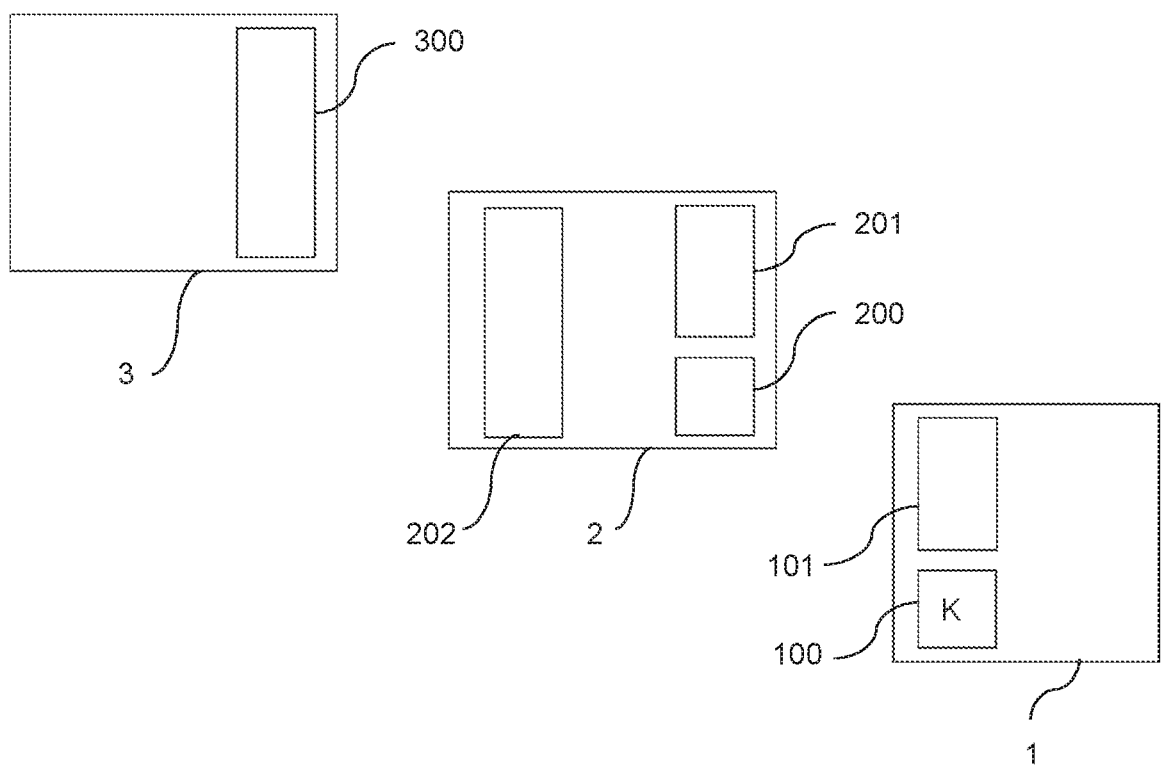
FIGS. 7 to 9 illustrate different states of the system of FIG. 2 as a function of the pairing between the implant and the remote controller.

FIG. 7 represents the state of the system of FIG. 2 before pairing. The implant 1 is provided with a secrete key 100 the value of which is denoted as K, the value of the secrete key 200 of remote controller 2 being not yet defined.

To enable the patient to subsequently communicate with his/her implant by means of the remote controller, this has to be paired with the implant, that is the value of the secrete key of the remote controller should also be equal to K.

To that end, the following procedure is implemented by the user once the remote controller has been connected to the programming device.

First, the user selects a pairing request on the interface of the programming device.

By means of the reader of the programming device, the user reads the pairing code of the remote controller.

Still by means of the reader of the programming device, the user reads the pairing code of the implant. This code is sent to the remote controller by the programming device in order to carry out pairing between the remote controller and implant.

Once this pairing is validated, a communication is possible between the programming device and the implant through the remote controller.

The user can then program the operation of the implant from the programming device.

Once the implantation is ended, the remote controller is given to the patient which keeps it when he/she leaves hospital.

After Implantation (Use of the Patient's Remote Controller)

The user can communicate at any time with the implant through the remote controller. This is in particular the case when he/she wishes to activate or deactivate a function of the implant, recover information about the state of the implant (charge level of the battery optionally, etc.).

Furthermore, during a visit at the practitioner's, said practitioner may also need to communicate with the implant, for example to modify its programming, or to recover data of the implant (for example, charge level of the battery, patient's data recorded by one or more sensors integrated into the implant, etc.).

To that end, the practitioner has the programming device at his/her disposal.

First, a practitioner has to establish a connection (wire or wireless connection, depending on the chosen embodiment) between the remote controller and the programming device, and make the communication request by reading the pairing code of the remote controller by means of the reader of the programming device.

He/she can possibly display the parameters of the implant and/or of the patient on the user interface, which enables him/her to check that it is with the proper implant that the communication is going to be established. If the practitioner confirms the communication request, the communication session between the implant and the programming device, through the remote controller, starts.

Figure 8:
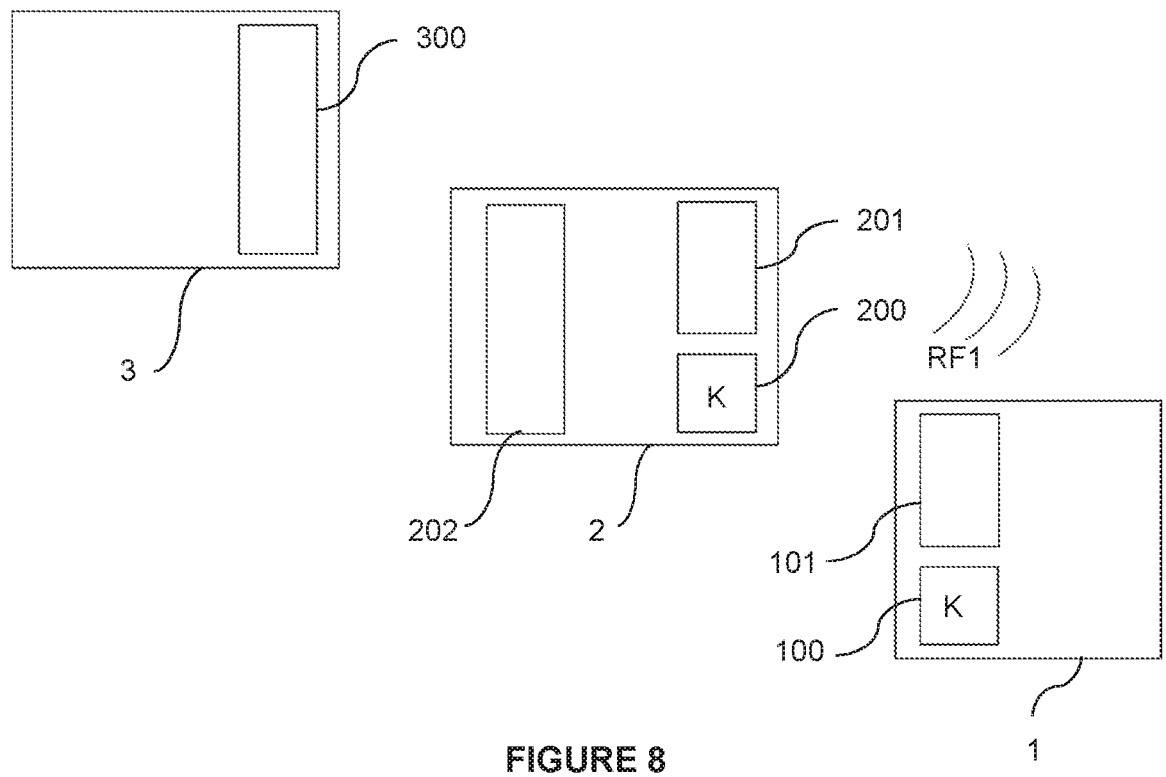

As illustrated in FIG. 8, it is the identity of the secrete keys 200 and 100 which enables a communication to be established between the remote controller 2 and the implant 1 and, if the remote controller 2 is connected to the programming device 3, between said programming device 3 and the implant 1 through the remote controller 2.

Figure 9:
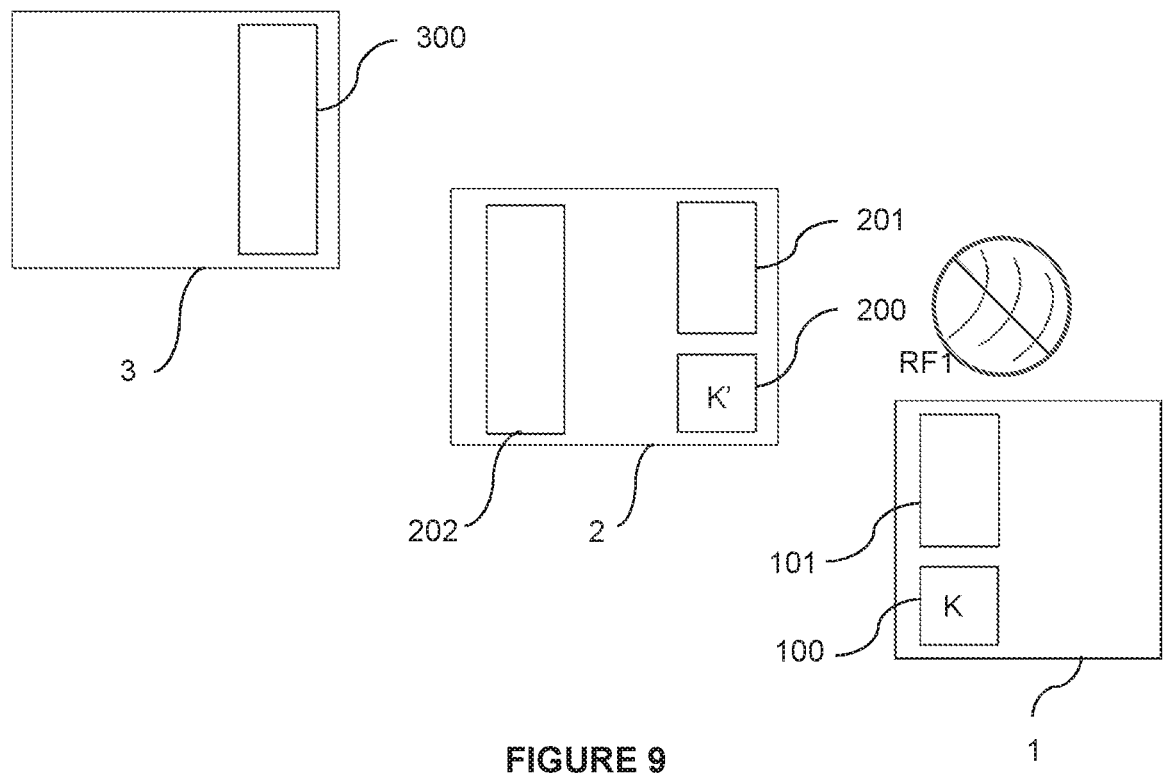

On the contrary, if, as illustrated in FIG. 9, an attempt is made to use a remote controller 2 the secrete key 200 of which has a value K' different from K, then no communication can be established between the remote controller 2 and the implant 1, and it will also be impossible to establish a communication between the programming device 3 and the implant 1.

After Implantation (Use of a New Remote Controller)

In some cases, the remote controller initially given to the patient may not be available, for example if he/she forgets, loses or damages the remote controller.

In this case, a new remote controller should be paired with the implant in order to be given to the patient.

Two situations may occur.

Normal Pairing Procedure

In the simpler situation, the pairing code of the implant is available (for example, displayed on the original package, or kept in the patient's file).

In this case, the pairing procedure is as follows.

First, the practitioner selects a pairing request on the user interface of the programming device.

The pairing code of the remote controller is read by the reader of the programming device (or input manually on the user interface). The communication between the remote controller and the programming device is then established.

Then, the pairing code of the implant is read by the reader of the programming device or input manually by the practitioner using the interface of the programming device. This code is then communicated to the remote controller to perform pairing.

Since the implant has another pairing code in memory, a confirmation request is displayed on the user interface of the programming device.

The practitioner has then to validate pairing between the new remote controller and the implant, for example by inputting a password on the user interface, or by tapping the implant according to a predetermined code.

Fail-Soft Pairing Procedure

However, it may occur that the pairing code of the implant is no longer available.

In this case, the practitioner selects a pairing request in fail-soft mode on the user interface of the programming device. Advantageously, the user interface displays a warning for the practitioner regarding the use of this pairing mode.

The pairing code of the remote controller is read by the reader of the programming device. The communication between the remote controller and the programming device is then established.

The remote controller detects the implants within reach, and the user interface displays parameters of each implant (for example, serial number, etc.).

In the case where several implants are present, the user selects the desired implant, for example by selecting its serial number from those provided.

Insofar as the implant has another pairing code in memory, a confirmation request is displayed on the user interface of the programming device.

The practitioner then has to validate the pairing between the new remote controller and the implant, for example by inputting a password on the user interface, or by tapping the implant according to a predetermined code.

The abovementioned pairing procedures can also be applied for the use of the "general purpose" remote controller available to the practitioner.

Of course, the examples just given are only particular and in no way limiting illustrations as far as the application fields of the invention are concerned.

The invention claimed is:

1. A telemetry communication system for an implantable medical device comprising a memory and a radiofrequency transceiver, comprising:
   a remote controller adapted to be used by a patient into whom said medical device is implanted, said remote controller comprising a memory and a radiofrequency transceiver configured to communicate with said implantable medical device in a first frequency band dedicated to implantable medical devices, the transceiver of the remote controller being paired with the transceiver of the implantable medical device such that the memory of the remote controller stores a pairing code associated with the implantable medical device and/or the memory of the implantable medical device stores a pairing code associated with said remote controller,
   a programming device for programming said implantable medical device adapted to be used by a practitioner, comprising a user interface, and configured to communicate with the remote controller through a wire connection or a wireless connection in a second frequency band dedicated to consumer applications, the second frequency band being different from the first frequency band,
   the programming device being configured to, when the wire or wireless connection is established between the remote controller and the programming device, establish a communication between the implantable medical device and the programming device through the remote controller,
   wherein the pairing code associated with the implantable device is also placed on the implantable device or on the package in which the implantable device is delivered before implantation of the implantable device into a patient and/or the pairing code associated with the remote controller is also placed on the remote controller or on the package in which the remote controller is delivered before implantation of the implantable device into a patient and wherein the programming device comprises a reader adapted to read said pairing code associated with the implantable device and/or said pairing code associated with said remote controller, or
   wherein the user interface of the programming device is adapted to allow a manual input by the practitioner of the pairing code associated with the implantable device and/or the pairing code associated with said remote controller.

2. The system of claim 1, wherein the programming device comprises a housing for plugging in the remote controller.

3. The system of claim 1, wherein the pairing code associated with the implantable device and/or the pairing code associated with the remote controller comprises a bar code.

4. The system of claim 1, wherein the reader is of the optical and/or near field communication type.

5. The system of claim 1, wherein the connection between the remote controller and the programming device is a wireless connection.

6. The system of claim 1, wherein the connection between the programming device and the remote controller is a wire connection, the programming device and the remote controller comprising respective connectors adapted to cooperate with each other.

7. The system of claim 1, wherein each of the remote controller and programming device comprises a microcontroller and the connection between the remote controller and the programming device comprises data transmission between said microcontrollers.

8. The system of claim 1, wherein the programming device comprises a microcontroller and the connection between the remote controller and the programming device comprises data transmission between said microcontroller and the transceiver of the remote controller.

9. The system of claim 1, wherein the remote controller comprises a microcontroller and the connection between the remote controller and the programming device comprises a data transmission between said microcontroller and the user interface of the programming device.

10. The system of claim 1, wherein the programming device is configured to display, on the user interface, information relating to a state of the remote controller when the remote controller is connected with said programming device.

11. The system of claim 1, wherein the connection between the remote controller and the programming device comprises supplying energy to the remote controller through the programming device.

12. The system of claim 1, wherein the first frequency band is a MICS (Medical Device Radiocommunications Service) band.

13. A method for communicating between an implantable medical device comprising a radiofrequency transceiver and a programming device of a telemetry communication system, wherein the telemetry communication system comprises:
   a remote controller adapted to be used by a patient into whom said medical device is implanted, said remote controller comprising a radiofrequency transceiver configured to communicate with said implantable medical device in a first frequency band dedicated to implantable medical devices, the transceiver of the remote controller being paired with the transceiver of the implantable medical device, and
   a programming device for programming said implantable medical device adapted to be used by a practitioner, comprising a user interface, and configured to communicate with the remote controller through a wire connection or a wireless connection in a second frequency band dedicated to consumer applications,
   the programming device being configured to, when the wire or wireless connection is established between the remote controller and the programming device, establish a communication between the implantable medical device and the programming device through the remote controller,
   the method comprising establishing a connection between the remote controller of said system and the programming device and establishing a communication between the programming device and the implantable medical device through the remote controller in a frequency band dedicated to implantable medical devices, further comprising, prior to establishing the communication between the programming device and the implantable medical device, a step of pairing the remote controller with the implantable medical device comprising:

inputting a pairing code on the programming device or reading the pairing code of the remote controller by the programming device, the pairing code associated with the remote controller being placed on the remote controller or on the package in which the remote controller is delivered before implantation of the implantable medical device into the patient, establishing a connection between the remote controller and the programming device, inputting a pairing code on the programming device or reading the pairing code of the implantable medical device by the programming device, the pairing code associated with the implantable medical device being placed on the implantable device or on the package in which the implantable medical device is delivered before implantation of the implantable medical device into the patient, and sending said code to the remote controller via the connection established between the remote controller and the programming device, validating pairing with said codes.

14. A method for communicating between an implantable medical device comprising a radiofrequency transceiver and a programming device of a telemetry communication system, wherein the telemetry communication system comprises:

a remote controller adapted to be used by a patient into whom said medical device is implanted, said remote controller comprising a radiofrequency transceiver configured to communicate with said implantable medical device in a first frequency band dedicated to implantable medical devices, the transceiver of the remote controller being paired with the transceiver of the implantable medical device, and a programming device for programming said implantable medical device adapted to be used by a practitioner, comprising a user interface, and configured to communicate with the remote controller through a wire connection or a wireless connection in a second frequency band dedicated to consumer applications, the programming device being configured to, when the wire or wireless connection is established between the remote controller and the programming device, establish a communication between the implantable medical device and the programming device through the remote controller, the method comprising establishing a connection between the remote controller of said system and the programming device and establishing a communication between the programming device and the implantable medical device through the remote controller in a frequency band dedicated to implantable medical devices, wherein, in the absence of the remote controller paired with the implantable medical device, another remote controller unpaired with said implantable medical device is used and the following steps are implemented:

reading a pairing code of said other remote controller by the programming device, or inputting said code on the programming device, establishing a connection between said other remote controller and the programming device, according to a first alternative, reading the pairing code of the implantable medical device, or inputting said code on the programming device, and sending said code to said other remote controller, or according to a second alternative, detecting at least one medical device within reach of said other remote controller, and selecting, by a user, the implantable medical device with which said other remote controller has to be paired, confirming, by a user, a pairing control order.

15. The method of claim 14 according to the first alternative, wherein confirming the pairing control order with the selected implantable medical device comprises performing a series of taps according to a predetermined code on the patient's skin facing the implantable medical device, said code being detected by a sensor of said device.

16. A method for communicating between an implantable medical device comprising a radiofrequency transceiver and a programming device of a telemetry communication system, wherein the telemetry communication system comprises:

a remote controller adapted to be used by a patient into whom said medical device is implanted, said remote controller comprising a radiofrequency transceiver configured to communicate with said implantable medical device in a first frequency band dedicated to implantable medical devices, the transceiver of the remote controller being paired with the transceiver of the implantable medical device, and a programming device for programming said implantable medical device adapted to be used by a practitioner, comprising a user interface, and configured to communicate with the remote controller through a wire connection or a wireless connection in a second frequency band dedicated to consumer applications, the programming device being configured to, when the wire or wireless connection is established between the remote controller and the programming device, establish a communication between the implantable medical device and the programming device through the remote controller, the method comprising establishing a connection between the remote controller of said system and the programming device and establishing a communication between the programming device and the implantable medical device through the remote controller in a frequency band dedicated to implantable medical devices, wherein, in the absence of the remote controller paired with the implantable medical device, a general purpose remote controller is used, configured to communicate with any implantable medical device of the same type and the following steps are implemented:

reading a pairing code of said general purpose remote controller by the programming device, establishing a connection between said general purpose remote controller and the programming device, detecting at least one medical device within reach of said general purpose remote controller, selecting, by a user, the implantable medical device with which the connection must be carried out, confirming, by the user the connection between said implantable medical device and the programming device.

17. The method of claim 16, wherein confirming the connection between the selected implantable medical device and the programming device comprises performing a series of taps according to a predetermined code on the patient's skin facing the implantable medical device, said code being detected by a sensor of said device.

* * * * *